(12) United States Patent
Koseoglu et al.

(10) Patent No.: US 11,066,609 B2
(45) Date of Patent: Jul. 20, 2021

(54) INTEGRATED METHODS AND SYSTEMS OF HYDRODEARYLATION AND HYDRODEALKYLATION OF HEAVY AROMATICS TO PRODUCE BENZENE, TOLUENE, AND XYLENES

(71) Applicant: Saudi Arabian Oil Company, Dhahran (SA)

(72) Inventors: Omer Refa Koseoglu, Dhahran (SA); Robert Peter Hodgkins, Dhahran (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 0 days.

(21) Appl. No.: 16/672,254

(22) Filed: Nov. 1, 2019

(65) Prior Publication Data

US 2021/0130709 A1    May 6, 2021

(51) Int. Cl.

| | |
|---|---|
| *C07C 4/26* | (2006.01) |
| *C10G 67/02* | (2006.01) |
| *C07C 4/24* | (2006.01) |
| *C07C 7/09* | (2006.01) |
| *C07C 7/00* | (2006.01) |
| *B01J 8/04* | (2006.01) |
| *B01J 10/00* | (2006.01) |

(Continued)

(52) U.S. Cl.
CPC .............. *C10G 67/02* (2013.01); *B01D 3/143* (2013.01); *B01J 8/0492* (2013.01); *B01J 10/00* (2013.01); *C07C 4/24* (2013.01); *C07C 4/26* (2013.01); *C07C 7/005* (2013.01); *C07C 7/04* (2013.01); *C07C 7/09* (2013.01); *C10G 2300/202* (2013.01); *C10G 2300/301* (2013.01); *C10G 2400/30* (2013.01)

(58) Field of Classification Search
CPC .. C07C 4/26; C07C 15/08; C07C 4/24; C07C 6/126; C07C 15/00; C07C 15/04; C07C 4/18; C07C 4/22; C10G 69/06; C10G 69/00; C10G 69/08; C10G 35/14; C10G 45/64; C10G 47/16; C10G 59/02
See application file for complete search history.

(56) References Cited

U.S. PATENT DOCUMENTS

| | | |
|---|---|---|
| 2,697,684 A | 12/1954 | Hemminger et al. |
| 3,145,238 A | 8/1964 | Newton |
| 3,150,196 A | 9/1964 | Mason, Jr. |

(Continued)

FOREIGN PATENT DOCUMENTS

| | | |
|---|---|---|
| CN | 103121895 B | 6/2015 |
| EP | 2773602 B1 | 7/2017 |

(Continued)

OTHER PUBLICATIONS

U.S. Appl. No. 16/592,591, "Two Stage Hydrodearylation Systems and Processes to Convert Heavy Aromatics Into Gasoline Blending Components and Chemical Grade Aromatics", filed Oct. 10, 2019.

(Continued)

*Primary Examiner* — Sharon Pregler
(74) *Attorney, Agent, or Firm* — Bracewell LLP; Constance G. Rhebergen; Kevin R. Tamm (57) ABSTRACT

Provided here are systems and methods that integrate a hydrodearylation process and a hydrodealkylation process into an aromatic recovery complex. Various other embodiments may be disclosed and claimed.

27 Claims, 3 Drawing Sheets

(51) Int. Cl.
  *B01D 3/14* (2006.01)
  *C07C 7/04* (2006.01)

(56) References Cited

U.S. PATENT DOCUMENTS

| | | | |
|---|---|---|---|
| 3,485,883 | A | 12/1969 | Engelbrecht et al. |
| 3,957,621 | A | 5/1976 | Bonacci et al. |
| 4,031,154 | A | 6/1977 | Edison et al. |
| 4,244,808 | A | 1/1981 | Lang et al. |
| 4,806,700 | A | 2/1989 | Martindale |
| 8,932,451 | B2 | 1/2015 | Strauss et al. |
| 9,909,075 | B2 | 3/2018 | Klein et al. |
| 10,053,401 | B1 * | 8/2018 | Beadle ............... C07C 4/26 |
| 10,093,873 | B2 | 10/2018 | Koseoglu et al. |
| 2015/0141724 | A1 | 5/2015 | Frey et al. |
| 2019/0241486 | A1 | 8/2019 | Koseoglu et al. |

FOREIGN PATENT DOCUMENTS

| | | |
|---|---|---|
| EP | 3539651 A1 | 9/2019 |
| GB | 1020595 A | 2/1966 |
| GB | 1148200 A | 4/1969 |
| WO | 2018127812 A1 | 7/2018 |
| WO | 2018152389 A1 | 8/2018 |

OTHER PUBLICATIONS

U.S. Appl. No. 16/594,768, "Catalytic Hydrodearylation of Heavy Aromatic Stream Containing Dissolved Hydrogen", filed Oct. 7, 2019.
U.S. Appl. No. 16/600,055, "Systems and Processes to Deolefinate Aromatic-Rich Hydrocarbon Streams", filed Oct. 11, 2019.
U.S. Appl. No. 16/600,285, "Methods and Systems of Upgrading Heavy Aromatics Stream to Petrochemical Feedstock", filed Oct. 11, 2019.
U.S. Appl. No. 16/672,052, "Methods and Systems of Upgrading Heavy Aromatics Stream to Petrochemical Feedstock", filed Nov. 1, 2019.
International Search Report and Written Opinion for related PCT application PCT/US2020/028614 dated Jul. 15, 2020.
International Search Report and Written Opinion for related PCT application PCT/US2020/058042, dated Feb. 10, 2021.
International Search Report and Written Opinion for PCT Application No. PCT/US2020/057907 dated Feb. 23, 2021.

* cited by examiner

FIG. 3

INTEGRATED METHODS AND SYSTEMS OF HYDRODEARYLATION AND HYDRODEALKYLATION OF HEAVY AROMATICS TO PRODUCE BENZENE, TOLUENE, AND XYLENES

TECHNICAL FIELD

The disclosure relates to production of benzene, toluene, and xylenes from an aromatic recovery process.

BACKGROUND

In an aromatics complex, a variety of process units are used to convert naphtha or pyrolysis gasoline into benzene, toluene and mixed xylenes, which are basic petrochemical intermediates used for the production of various other chemical products. In order to increase the production of benzene and xylenes, the toluene and $C_9$ and $C_{10}$ aromatics are processed within the complex through a toluene, $C_9$, $C_{10}$ transalkylation/toluene disproportionation (TA/TDP) process unit to produce benzene and xylenes. Any remaining toluene, $C_9$, and $C_{10}$ aromatics are recycled to extinction. Compounds heavier than $C_{10}$ are generally not processed in the TA/TDP unit, as they tend to cause rapid deactivation of the catalysts used at the higher temperatures applied in these units, often greater than 400° C.

When para-xylene is recovered from mixed xylenes by a selective adsorption process unit in the complex, the $C_8$ feed to the selective adsorption unit is processed to eliminate olefins and alkenyl aromatics such as styrene in the feed. Olefinic material can react and occlude the pores of the zeolite adsorbent. The olefinic material is removed by passing a $C_{8+}$ stream across a clay or acidic catalyst to react olefins and alkenyl aromatics with another (typically aromatic) molecule, forming heavier compounds ($C_{16+}$). These heavier compounds are typically removed from the mixed xylenes by fractionation. The heavy compounds cannot be processed in the TA/TDP unit due to their tendency to deactivate the catalyst and are generally removed from the complex as lower value fuels blend stock. As many of the heavy alkyl aromatic compounds fractionate with the fractions containing greater than 10 carbon atoms, they are not typically sent as feedstock to the transalkylation unit, and instead are sent to gasoline blending or used as fuel oil.

SUMMARY

A need has been recognized for the production of monoaromatics from certain heavy compounds formed during the treatment of aromatics streams during processing of hydrocarbons. Certain embodiments include integrated methods and systems for production of benzene, toluene, and xylenes that include hydrodearylation and hydrodealkylation. In an embodiment, the hydrodealkylation is a non-catalytic hydrodealkylation, such as thermal hydrodealkylation. An embodiment of the process for production of benzene, toluene, and xylenes includes the following steps: (a) supplying a hydrogen stream and a feed stream containing one or more of heavy alkyl aromatic compounds and alkyl-bridged non-condensed alkyl multi-aromatic compounds from an aromatic complex to a hydrodearylation reactor to react in presence of a catalyst under specific reaction conditions to yield a hydrodearylated stream containing hydrogen, $C_1$ to $C_4$ gases, benzene, toluene, xylenes, and $C_{9+}$ compounds; (b) supplying the hydrodearylated stream to a first separation unit to produce a bottom separated stream containing $C_{9+}$ compounds and a top separated stream containing hydrogen, $C_1$ to $C_4$ gases, benzene, toluene, and xylenes; (c) supplying a hydrogen stream and the bottom separated stream containing $C_{9+}$ compounds to a hydrodealkylation reactor to produce a hydrodealkylated stream containing $C_1$ to $C_4$ gases, benzene, toluene, and xylenes; and (d) supplying the hydrodealkylated stream to a second separation unit to produce a bottom product stream containing unconverted $C_{9+}$ compounds and a top product stream containing hydrogen, $C_1$ to $C_4$ gases, benzene, toluene, and xylenes.

In an embodiment, the hydrodealkylation reactor is a non-catalytic thermal hydrodealkylation reactor. In an embodiment, conditions in the hydrodealkylation reactor include an operating temperature in the range of about 500 to 900° C. In an embodiment, conditions in the hydrodealkylation reactor include an operating hydrogen partial pressure in the range of about 5 bar gauge to 100 bar gauge. In an embodiment, a molar ratio of hydrogen to the hydrocarbon components in the hydrodealkylation reactor ranges from about 1 to 20.

In an embodiment, conditions in the hydrodearylation reactor include an operating temperature in the range of about 200 to 450° C. In an embodiment, conditions in the hydrodearylation reactor include an operating pressure in the range of about 5 bar gauge to 80 bar gauge. In an embodiment, a volumetric ratio of hydrogen to the hydrocarbon components in the hydrodearylation reactor ranges from about 50 to 2500 $Nm^3/m^3$. In an embodiment, the catalyst includes a support being at least one member of the group consisting of silica, alumina, titania, and combinations thereof, and further includes an acidic component being at least one member of the group consisting of amorphous silica-alumina, alumina, zeolite, and combinations thereof.

In an embodiment, the top product stream, in addition to or alternative to the top separated stream, is supplied to an aromatic fractionation unit to produce a benzene-rich stream, a toluene-rich stream, and a xylene-rich stream. A sulfur-containing compound that can decompose to yield hydrogen sulfide, for example disulfide oils with 2 to 10 carbon number, for example dimethyldisulfide, can be supplied to the hydrodealkylation reactor. The bottom product stream can be recycled to the hydrodealkylation reactor or to the hydrodearylation reactor. In an embodiment, the feed stream is from a xylene rerun column of an aromatic recovery process.

An embodiment of a system for production of benzene, toluene, and xylenes includes the following: (a) a hydrodearylation reactor adapted to receive a hydrogen stream and a feed stream containing one or more of heavy alkyl aromatic compounds and alkyl-bridged non-condensed alkyl multi-aromatic compounds and to produce a hydrodearylated stream in presence of a catalyst, and the hydrodearylated stream containing one or more alkyl mono-aromatic compounds; (b) a first separator fluidly coupled to the hydrodearylation reactor and adapted to receive the hydrodearylated stream and to produce a bottom separated stream containing $C_{9+}$ compounds and a top separated stream containing hydrogen, $C_1$ to $C_4$ gases, benzene, toluene, and xylenes; (c) a hydrodealkylation reactor that is adapted to receive the bottom separated stream containing the $C_{9+}$ compounds and to produce a hydrodealkylated stream containing $C_1$ to $C_4$ gases, benzene, toluene, and xylenes; and (d) a second separator fluidly coupled to the hydrodealkylation reactor and adapted to receive the hydrodealkylated stream and to produce a bottom product stream containing unconverted $C_{9+}$ compounds and a top product stream containing hydrogen, $C_1$ to $C_4$ gases, benzene, toluene, and xylenes. The hydrodealkylation reactor can be a non-catalytic thermal hydrodealkylation reactor.

In an embodiment, the system includes an aromatic fractionation unit fluidly coupled to the second separator and adapted receive the top product stream and to produce a benzene-rich stream, a toluene-rich stream, a xylene-rich stream. The hydrodealkylation reactor can be further adapted to receive a sulfur-containing compound that can decompose to yield hydrogen sulfide, for example disulfide oils with 2 to 10 carbon number, for example dimethyldisulfide. The hydrodealkylation reactor can be further adapted to receive a portion of the bottom product stream from the second separator. The hydrodearylation reactor can be further adapted to receive a portion of the bottom product stream from the second separator.

In certain embodiments disclosed throughout, a hydrodearylation unit is not required preceding the hydrodealkylation unit, and in certain other embodiments a separation unit is not required between hydrodearylation and hydrodealkylation reaction units.

BRIEF DESCRIPTION OF THE DRAWINGS

Embodiments will be readily understood by the following detailed description in conjunction with the accompanying drawings. Embodiments are illustrated by way of example and not by way of limitation in accompanying drawings.

DETAILED DESCRIPTION

The present disclosure describes various embodiments related to processes, devices, and systems for conversion of a rejects stream from an aromatic recovery complex consisting of long chain alkyl monoaromatics and bridged diaromatics to produce benzene, toluene and xylenes. Further embodiments are described and disclosed.

In the following description, numerous details are set forth in order to provide a thorough understanding of the various embodiments. In other instances, well-known processes, devices, and systems may not have been described in particular detail in order not to unnecessarily obscure the various embodiments. Additionally, illustrations of the various embodiments may omit certain features or details in order to not obscure the various embodiments. Here, reference is made to the accompanying drawings that form a part of this disclosure. The drawings may provide an illustration of some of the various embodiments in which the subject matter of the present disclosure may be practiced. Other embodiments may be utilized, and logical changes may be made without departing from the scope of this disclosure. Therefore, the following detailed description is not to be taken in a limiting sense.

The description may use the phrases "in some embodiments," "in various embodiments," "in an embodiment," or "in embodiments," which may each refer to one or more of the same or different embodiments. Furthermore, the terms "comprising," "including," "having," and the like, as used with respect to embodiments of the present disclosure, are synonymous.

As used in this disclosure, the term "hydrodearylation" refers to a process for cleaving of the alkyl bridge of non-condensed alkyl-bridged multi-aromatics or heavy alkyl aromatic compounds to form alkyl mono-aromatics and benzene, in the presence a catalyst and hydrogen.

As used in this disclosure, the term "hydrodealkylation" refers to the reaction of an alkyl aromatic compound with hydrogen to yield a lower molecular weight aromatic compound and a light paraffin gas by scission of the carbon-carbon bond between the aromatic ring and one or more paraffin attached to it. Examples of hydrodealkylation include the conversion of toluene to benzene and methane and the conversion of ethyl benzene to benzene and ethane.

As used in this disclosure, the term "stream" (and variations of this term, such as hydrocarbon stream, feed stream, product stream, and the like) may include one or more of various hydrocarbon compounds, such as straight chain, branched or cyclical alkanes, alkenes, alkadienes, alkynes, alkyl aromatics, alkenyl aromatics, condensed and non-condensed di-, tri- and tetra-aromatics, and gases such as hydrogen and methane, $C_{2+}$ hydrocarbons and further may include various impurities.

As used in this disclosure, the term "rich" means an amount of at least 30% or greater, by mole percentage of a compound or class of compounds in a stream. Certain streams rich in a compound or class of compounds can contain about 50% or greater, by mole percentage of the particular compound or class of compounds in the streams. In certain cases, mole percentage may be replaced by weight percentage, in accordance with standard industry usage.

As used in this disclosure, the term "mixed xylenes" refers to a mixture containing one or more $C_8$ aromatics, including any one of the three isomers of di-methylbenzene and ethylbenzene.

Processing of hydrocarbons leads to the production of compounds containing an aromatic ring with one or more coupled alkyl groups. As many of these heavy alkyl aromatic compounds fractionate with the $C_{11+}$ fractions, they are sent to gasoline blending or to be used as fuel oil. $C_9$ and $C_{10}$ compounds can be sent to a TA/TDP. Hydrocarbon compounds heavier than $C_{10}$ are not typically processed in the TA/TDP. The methods and systems disclosed here result in upgrading a low value fuel oil to premium value products, such as benzene, toluene, and xylenes, and an aromatics- and benzene-free gasoline blending component.

Catalytic reformers produce reformate, an aromatic rich gasoline blending fraction or feedstock for BTX production. The aromatic complex produces a $C_{9+}$ reject stream or bottoms containing multiple aromatic rings or mono-aromatic compounds with multiple and/or heavy ($C_{3+}$) alkyl groups whose boiling point ranges from 100° C.-450° C. The reject stream is not suitable as a gasoline blending component. Due to the stringent fuel specifications implemented or being implemented worldwide, requiring less than 35 volume percent (vol. %) of BTX and less than 1 vol. % of benzene in gasoline, the reformate fraction has to be further treated to reduce its aromatics content. The reformate fraction can be subject to benzene hydrogenation or BTX extraction. In the benzene hydrogenation process, the reformate is hydrogenated to reduce the benzene content and the total BTX content is reduced by blending if needed. In the BTX extraction process, the reformate is sent to an aromatic complex to extract benzene, toluene, and xylenes, which have a premium value, and to produce an aromatics- and benzene-free gasoline blending component. This disclosure is directed to methods and systems of increasing the yield of benzene, toluene, and xylenes by integrating a catalytic hydrodearylation process and a non-catalytic hydrodealkylation process.

Disclosed here is a method of processing an aromatic rejects stream containing long chain alky monoaromatics and bridged diaromatics, which is a byproduct of an aromatic recovery complex. The aromatic rejects stream is supplied to a catalytic hydrodearylation reactor, where the long chain alky monoaromatics and bridged diaromatics are converted to monoaromatic compounds. This stream containing the monoaromatic compounds is supplied to a separation unit, where the $C_1$-$C_4$ gases, benzene, xylenes and toluene and other components are separated from the fraction containing the $C_{9+}$ compounds. This fraction containing the $C_{9+}$ compounds is then supplied to a non-catalytic thermal hydrodealkylation step to dealkylate monoaromatics to produce a benzene-containing stream. This benzene-containing stream is sent to a second separation unit to obtain a benzene-rich stream.

An embodiment of this disclosure is a method of production of benzene, toluene, and xylenes from a feed stream containing $C_{9+}$ compounds from an aromatic complex. The method includes subjecting the aromatic rejects stream from the aromatics complex to an integrated hydrodearylation and a thermal hydrodealkylation processes. The hydrodealkylation of toluene is an exothermic reaction with a heat release of 12.1 kilocalories per gram mole (Kcal/g·mol), which is similar to that of hydrodesulfurization. Non-catalytic hydrodealkylation is carried out at temperatures ranging from 500° C. to 750° C., pressures ranging from 14 to 60 bars and with a residence time of 10 to 100 seconds. The molar ratio of hydrogen to the aromatics ranges from 3 to 8. Hydrodealkylation reactions of heavy aromatics ($C_8$-$C_{10}$) proceed at a substantially faster rate than that of toluene. Thermal hydrodealkylation produces products of extremely high purity because substantially all $C_3$ and heavier paraffins and other saturated compounds are hydrocracked under severe conditions. The products of this hydrocracking are methane and ethane. However, these reactions consume large quantities of hydrogen resulting in an increase in the exotherm and hydrogen consumption. High purity benzene production suggests that the equilibrium between cyclohexane and benzene is towards benzene production.

Catalytic hydrodealkylation takes place at the same pressures as thermal reactors, but at much lower temperatures, such as 600° C. At lower temperatures, the thermodynamic equilibrium indicates that cyclohexane is formed which contaminates the final benzene product. Catalytic hydrodealkylation requires frequent regeneration of the catalyst. In both thermal and catalytic processes, another reaction is aromatic ring condensation to form poly nuclear aromatics that tend to form coke, which results in fouling in the downstream of the equipment.

In a typical refinery with an aromatic complex, the whole crude oil is distilled in an atmospheric distillation column to recover a naphtha fraction (compounds with a boiling point ranging from 36° C. to 180° C.), a diesel fraction (compounds with a boiling point ranging from 180° C. to 370° C.), and an atmospheric residue fraction (compounds with a boiling point of 370° C. and higher). The naphtha fraction is hydrotreated in a naphtha hydrotreating unit to produce a hydrotreated naphtha fraction that has a sulfur and nitrogen content of less than 0.5 parts per million weight (ppmw). This hydrotreated naphtha fraction is sent to a catalytic reforming unit to improve properties, such as an increase in the octane number to produce gasoline blending stream or feedstock for an aromatics recovery unit. The reformate fraction from this catalytic reforming unit can be used as a gasoline blending component or sent to an aromatic complex to recover benzene, toluene, and xylenes. The diesel fraction is hydrotreated in a separate hydrotreating unit to desulfurize the diesel fraction to obtain diesel oil that contains less than 10 ppm of sulfur. The atmospheric residue fraction is either used a fuel oil component or sent to other separation/conversion units to convert the low value hydrocarbon components to high value products. In an aromatic recovery complex, the reformate from the catalytic reforming unit is separated into two fractions: a light reformate containing $C_5$ to $C_7$ compounds and a heavy reformate containing $C_{8+}$ compounds. The light reformate is sent to a benzene extraction unit to extract the benzene and recover substantially benzene-free gasoline, along with toluene. The heavy reformate stream is sent to a p-xylene extraction unit to recover p-xylene. Other xylenes are recovered and sent to a xylene isomerization unit to convert them to p-xylene. The converted fraction is recycled to the p-xylene extraction unit. The heavy $C_{9+}$ fraction from the xylene re-run unit is recovered as process reject or bottoms. The aromatic rejects stream is directed to an integrated two-stage hydrodearylation and hydrodealkylation processing to increase BTX yield.

In an embodiment, the process reject or bottoms is supplied (either whole or fractionated) as feedstock along with an excess of hydrogen gas in a mixing unit before being supplied to a hydrodearylation reactor. A portion of the hydrogen gas is mixed with the feedstock to produce a hydrogen-enriched liquid hydrocarbon feedstock. This hydrogen-enriched liquid hydrocarbon feedstock and undissolved hydrogen is supplied to a flashing unit in which at least a portion of undissolved hydrogen is flashed, and the hydrogen is recovered and recycled. The hydrogen-enriched liquid hydrocarbon feedstock from the flashing unit is supplied as a feed stream to the hydrodearylation reactor.

Operating pressure conditions of the hydrodearylation reactor range from 5 bar to 80 bar. In certain embodiments, the operating pressure conditions of the hydrodearylation reactor range from 10 bar to 80 bar. In certain embodiments, the operating pressure conditions of the hydrodearylation reactor range from 15 bar to 40 bar. Operating temperature conditions of the hydrodearylation reactor range from 200° C. to 450° C. In certain embodiments, the operating temperature conditions of the hydrodearylation reactor range from 250° C. to 425° C. In certain embodiments, the operating temperature conditions of the hydrodearylation reactor range from 300° C. to 400° C. Residence time of the aromatic rejects stream in the hydrodearylation reactor ranges from 0.1 to 5 hours. In certain embodiments, the residence time of the aromatic rejects stream in the hydrodearylation reactor ranges from 0.5 to 3 hours. In certain embodiments, the residence time of the aromatic rejects stream in the hydrodearylation reactor ranges from 1 to 2 hours. The volumetric ratio of hydrogen to the hydrocarbon components in the hydrodearylation reactor ranges can range from 500 to 5000 standard cubic feet per barrel of hydrocarbon in the feed stream. In certain embodiments, the volumetric ratio of hydrogen to the hydrocarbon components in the hydrodearylation reactor ranges from 50 to 1000 standard cubic feet per barrel of hydrocarbon in the feed stream. In certain embodiments, the volumetric ratio of hydrogen to the hydrocarbon components in the hydrodearylation reactor ranges from 50 to 500 standard cubic feet per barrel of hydrocarbon in the feed stream. The specific reaction conditions can include a feed rate of the hydrogen stream that is in the range of 100 to 1000 standard liter per liter of feedstock. The specific reaction conditions can include a feed rate of the hydrogen stream that is in the range of 100 to 300 standard liter per liter of feedstock.

In certain embodiments, the hydrogen stream is combined with the feed stream before being supplied to the hydrodearylation reactor. In certain embodiments, the hydrogen stream includes a recycled hydrogen stream and a makeup hydrogen stream. In certain embodiments, the hydrogen stream comprises at least 70% hydrogen by weight. The catalyst can be presented as a catalyst bed in the reactor. In certain embodiments, a portion of the hydrogen stream is fed to the catalyst bed in the reactor to quench the catalyst bed. In certain embodiments, the catalyst bed is comprised of two or more catalyst beds. The catalyst can include a support that is at least one member of the group consisting of silica, alumina, titania, and combinations thereof, and further includes an acidic component that is at least one member of the group consisting of amorphous silica-alumina, zeolite, and combinations thereof. The zeolite can be one or more of or derived from FAU, *BEA, MOR, MFI, or MWW framework types, wherein each of these codes correspond to a zeolite structure present in the database of zeolite structures as maintained by the Structure Commission of the International Zeolite Association. In certain embodiments, the catalyst includes an IUPAC Group 8-10 metal and an IUPAC Group 6 metal. In certain embodiments, the catalyst includes an IUPAC Group 8-10 metal that is at least one member of the group consisting of iron, cobalt, and nickel, and combinations thereof. The catalyst includes an IUPAC Group 6 metal that is at least one member of the group consisting of molybdenum and tungsten, and combinations thereof. In certain embodiments, the IUPAC Group 8-10 metal is 2 to 20 percent by weight of the catalyst and the IUPAC Group 6 metal is 1 to 25 percent by weight of the catalyst. In certain embodiments, the catalyst is comprised of nickel, molybdenum, ultrastable Y-type zeolite, and silica-alumina support.

The hydrodearylated stream that is recovered from the hydrodearylation reactor contains hydrogen, $C_1$ to $C_4$ gases, BTX, and $C_{9+}$ compounds and is further processed as provided here. The hydrodearylated stream is supplied to a separation unit and is separated into a top separated stream and a bottom separated $C_{9+}$ stream. The top separated stream contains hydrogen, $C_1$ to $C_4$ gases, and hydrocarbons boiling in the range 26-180° C. including BTX. The bottom separated $C_{9+}$ stream generally boiling higher than 180° C. is supplied to a hydrodealkylation reactor along with a hydrogen stream, a steam stream, and a sulfur-containing compound stream that can decompose to yield hydrogen sulfide, for example disulfide oils with 2 to 10 carbon number, for example dimethyldisulfide. For the hydrodealkylation reactor, a hydrogen stream can be supplied at a hydrogen to aromatic ratio (mol:mol) of about 1:20, about 1:10, or about 3:8. The steam stream can be supplied at a steam to oil ratio (V %/V %) of about 0.1:1, about 0.01:1 or about 0.001:1. A hydrogen sulfide stream (which is generated by the decomposition of disulfide oils such as dimethyldisulfide, mercaptans and other sulfur-containing compounds) can be supplied with hydrogen sulfide (ppmw) at about 1-1000, about 1-100, or about 10-100. Hydrogen need not be supplied to a hydrodealkylation reactor in some embodiments if the hydrogen partial pressure in the feed to the hydrodealkylation reactor is sufficient from initial hydrogen injection at the hydrodearylation reactor.

Operating pressure conditions of the hydrodealkylation reactor range from 5 bar to 100 bar. In certain embodiments, the operating pressure conditions of the hydrodealkylation reactor range from 10 bar to 60 bar. In certain embodiments, the operating pressure conditions of the hydrodealkylation reactor range from 20 bar to 40 bar. Operating temperature conditions of the hydrodealkylation reactor range from 500° C. to 900° C. In certain embodiments, the operating temperature conditions of the hydrodealkylation reactor range from 600° C. to 800° C. In certain embodiments, the operating temperature conditions of the hydrodealkylation reactor range from 650° C. to 750° C. Residence time of the hydrodearylated stream in the hydrodealkylation reactor ranges from 1 to 1000 seconds. In certain embodiments, the residence time of the hydrodearylated stream in the hydrodealkylation reactor ranges from 10 to 500 seconds. In certain embodiments, the residence time of the hydrodearylated stream in the hydrodealkylation reactor ranges from 10 to 100 seconds. The molar ratio of hydrogen to the hydrocarbon components in the hydrodealkylation reactor ranges from 1 to 20. In certain embodiments, the molar ratio of hydrogen to the hydrocarbon components in the hydrodealkylation reactor ranges from 1 to 10. In certain embodiments, the molar ratio of hydrogen to the hydrocarbon components in the hydrodealkylation reactor ranges from 3 to 8.

Hydrogen sulfide is generated from disulfide oils, such as dimethyldisulfide, mercaptans, and other sulfur containing compounds. Hydrogen sulfide prevents coke formation in the hydrodealkylation reactor. The hydrogen sulfide concentration at the end of the hydrodealkylation process ranges from 1 to 1000 ppmw. In certain embodiments, the hydrogen sulfide concentration at the end of the hydrodealkylation process ranges from 1 to 100 ppmw. In certain embodiments, the hydrogen sulfide concentration at the end of the hydrodealkylation process ranges from 10 to 100 ppmw.

The hydrodearylated stream is processed in the hydrodealkylation reactor to produce a hydrodealkylated stream containing hydrogen, $C_1$ to $C_4$ gases, BTX, and residual $C_{9+}$ compounds. In an example product stream, $H_2$ can be present from about 0.01-5 wt. %, or from about 0.1-5 wt. %; C1-C4 gases can be present from about 0.01-5 wt. %, or from about 0.1-5 wt. %; BTX can be present from about 0.1-30 wt. %, or about 1-30 wt. %, and $C_{9+}$ can be present from about 70-99 wt. %. In certain embodiments, this hydrodealkylated stream is sent to a second separation unit to obtain a top product stream (containing hydrogen, $C_1$ to $C_4$ gases, and BTX) and a bottom product stream containing $C_{9+}$. In certain embodiments, the top product stream is sent to a fractionator to separate $C_1$ to $C_4$ gases and BTX. The BTX can be supplied to a benzene extraction unit to produce a benzene-rich stream and a stream containing the xylenes that can be processed to recover xylenes.

In an embodiment, a system is provided for conversion of alkyl-bridged non-condensed alkyl multi-aromatic compounds to benzene, toluene, and xylenes. This system includes the following: (a) a hydrodearylation reactor adapted to receive a hydrogen stream and a feed stream containing one or more of heavy alkyl aromatic compounds and alkyl-bridged non-condensed alkyl multi-aromatic compounds and to produce a hydrodearylated stream in presence of a catalyst, and the hydrodearylated stream containing one or more alkyl mono-aromatic compounds; (b) a first separator fluidly coupled to the hydrodearylation reactor and adapted to receive the hydrodearylated stream and to produce a bottom separated stream containing $C_{9+}$ compounds and a top separated stream containing hydrogen, $C_1$ to $C_4$ gases, benzene, toluene, and xylenes; (c) a hydrodealkylation reactor that is adapted to receive the bottom separated stream containing the $C_{9+}$ compounds and to produce a hydrodealkylated stream containing $C_1$ to $C_4$ gases, benzene, toluene, and xylenes; and (d) a second separator fluidly coupled to the hydrodealkylation reactor and adapted to receive hydrodealkylated stream and to produce a bottom product stream containing unconverted $C_{9+}$ compounds and a top product stream containing hydrogen, $C_1$ to $C_4$ gases, benzene, toluene, and xylenes. The hydrodealkylation reactor can be a non-catalytic thermal hydrodealkylation reactor. In certain embodiments, this top product, in addition to or alternative to the top separated stream, is sent to a third separation unit to obtain a benzene-rich stream.

Figure 1:
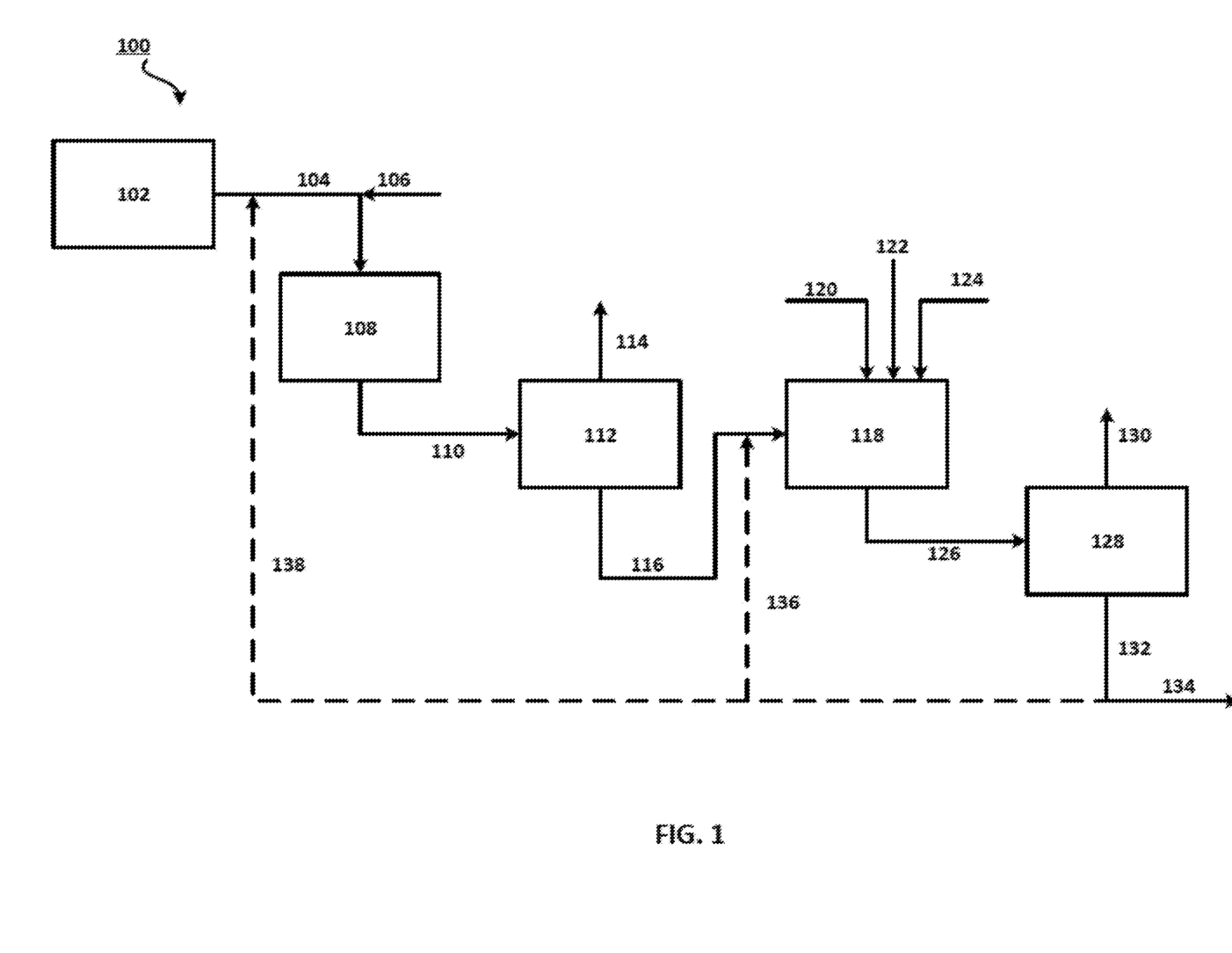
FIG. 1 is a schematic representation of integrated hydrodearylation and hydrodealkylation components of an aromatics processing system.

In an embodiment 100 as described in FIG. 1, an aromatic bottoms stream 104 from an aromatic recovery complex 102 and a hydrogen stream 106 are directed to a hydrodearylation reactor 108 for processing into a hydrodearylated stream 110. In some embodiments (not pictured) hydrogen gas can be dissolved in stream 104 and sent to a flash separator to leave only hydrogen dissolved in the liquid stream and any excess hydrogen gas recycled. In an embodiment, the hydrodearylated stream 110 contains greater than 10 wt. % of alkyl mono-aromatic compounds. In an embodiment, the hydrodearylated stream 110 contains greater than 20 wt. % of alkyl mono-aromatic compounds. In an embodiment, the hydrodearylated stream 110 contains greater than 40 wt. % of alkyl mono-aromatic compounds. In an embodiment, the hydrodearylated stream 110 contains about 50 wt. % of alkyl mono-aromatic compounds. In an embodiment, the hydrodearylated stream 110 contains about 70 wt. % of alkyl mono-aromatic compounds. Hydrodearylated stream 110 can also include benzene.

In an embodiment, the hydrodearylated stream 110 contains about 90 wt. % of alkyl mono-aromatic compounds. In an embodiment, the hydrodearylated stream 110 contains less than 70 wt. % of di-aromatic compounds. In an embodiment, the hydrodearylated stream 110 contains less than 50 wt. % of di-aromatic compounds. In an embodiment, the hydrodearylated stream 110 contains less than 40 wt. % of di-aromatic compounds. In an embodiment, the hydrodearylated stream 110 contains less than 20 wt. % of di-aromatic compounds. In an embodiment, the hydrodearylated stream 110 contains less than 10 wt. % of di-aromatic compounds. In an embodiment, the hydrodearylated stream 110 contains less than 1 wt. % of di-aromatic compounds.

The hydrodearylated stream 110 is supplied to a first separation unit 112. This separation unit 112 includes one or more fractionation columns. An embodiment can include a distillation column with several theoretical trays or a flash vessel or a stripper. The hydrodearylated stream 110 is separated in the first separation unit 112 to produce a top separated stream 114 and a bottom separated stream 116 comprising $C_{9+}$ compounds. The top separated stream 114 contains containing hydrogen, $C_1$ to $C_4$ gases, benzene, toluene, and xylenes. In an embodiment, this top separated stream 114 is supplied to a benzene extraction unit to produce a benzene-rich stream and a stream containing the xylenes that can be processed to recover xylenes. The bottom separated stream 116 comprising $C_{9+}$ compounds is supplied to a hydrodealkylation reactor 118 along with a hydrogen stream 120, a steam stream 122, and a sulfur-containing compound stream 124, for example a sulfur-containing compound stream that can decompose to yield hydrogen sulfide, for example disulfide oils with 2 to 10 carbon number, for example dimethyldisulfide. In an embodiment, the sulfur-containing compound stream 124 is substituted by a disulfide oil stream commonly produced in a MEROX unit. The bottom separated stream 116 is processed in the hydrodealkylation reactor 118 to produce a hydrodealkylated stream 126 containing hydrogen, $C_1$ to $C_4$ gases, benzene, toluene, xylenes, and residual $C_{9+}$ compounds.

In certain embodiments, this hydrodealkylated stream 126 is sent to a second separation unit 128 to obtain a top product stream 130 containing hydrogen, $C_1$ to $C_4$ gases, benzene, toluene, and xylenes. The bottom product stream 132 from second separation unit 128 is either removed as a bleed stream 134 or sent to the hydrodealkylation reactor 118 as a first recycle stream 136 or sent to the hydrodearylation reactor 108 as a second recycle stream 138. In certain embodiments, the top product stream 130 is sent to a fractionator to separate $C_1$ to $C_4$ gases and BTX. The BTX can be supplied to an aromatics fractionation unit to produce a benzene-rich stream and a stream containing the xylenes that can be processed to recover xylenes.

In various embodiments, the lighter hydrocarbon stream may be processed to provide a recycled hydrogen stream. In various embodiments, the recycled hydrogen stream may be combined with a makeup hydrogen stream to provide the hydrogen stream to be supplied to the hydrodearylation and hydrodealkylation reactors.

Figure 2:
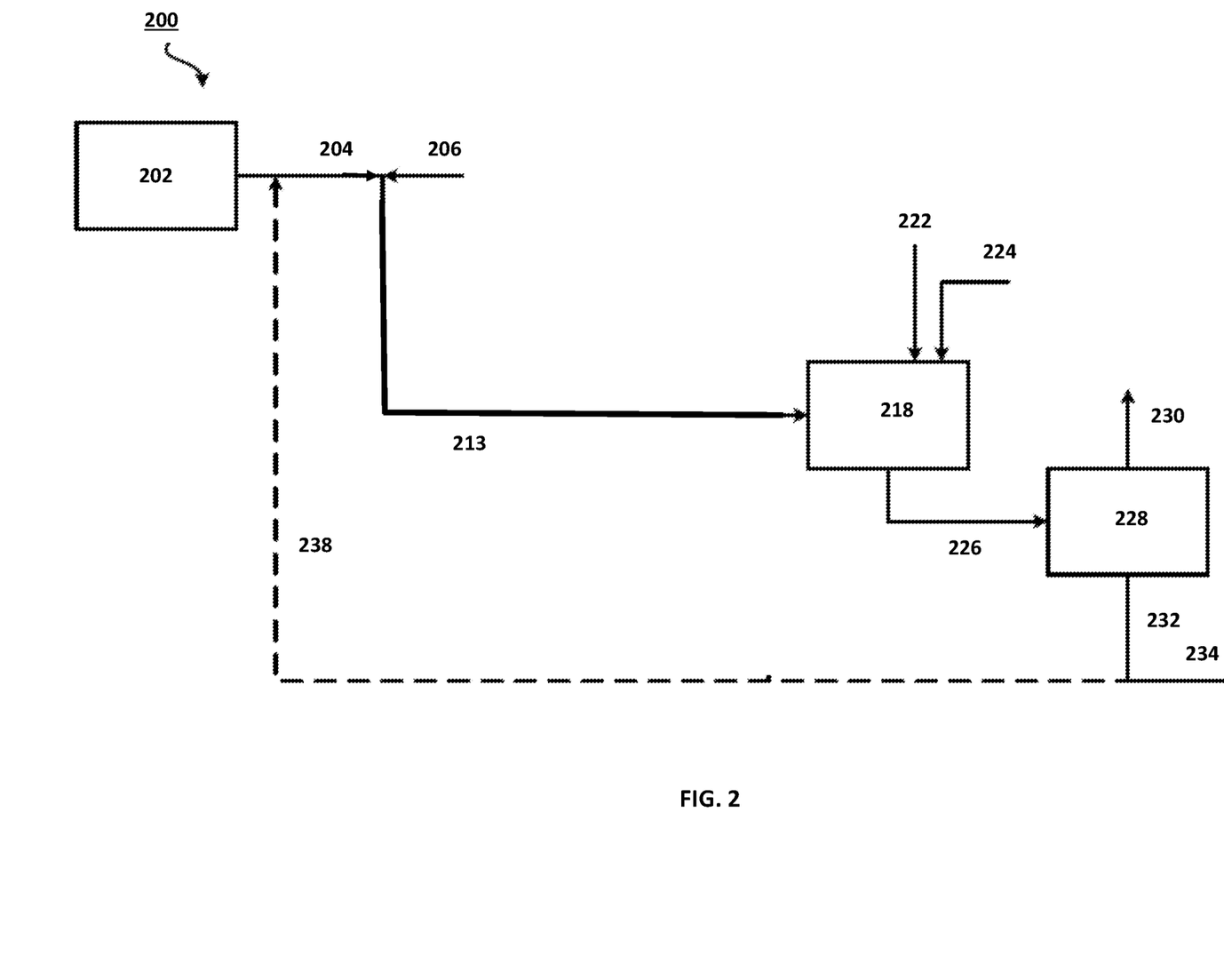
FIG. 2 is a schematic representation of integrated hydrodearylation and hydrodealkylation components of an aromatics processing system.

In an embodiment 200 as described in FIG. 2, an aromatic bottoms stream 204 from an aromatic recovery complex 202 and a hydrogen stream 206 are directed to a hydrodealkylation reactor 218, via hydrodealkylation inlet stream 213, for processing. In an embodiment, the hydrodealkylation inlet stream 213 contains greater than 10 wt. % of alkyl mono-aromatic compounds. In an embodiment, the hydrodealkylation inlet stream 213 contains greater than 20 wt. % of alkyl mono-aromatic compounds. In an embodiment, the hydrodealkylation inlet stream 213 contains greater than 40 wt. % of alkyl mono-aromatic compounds. In an embodiment, the hydrodealkylation inlet stream 213 contains about 50 wt. % of alkyl mono-aromatic compounds. In an embodiment, the hydrodealkylation inlet stream 213 contains about 70 wt. % of alkyl mono-aromatic compounds.

In an embodiment, the hydrodealkylation inlet stream 213 contains about 90 wt. % of alkyl mono-aromatic compounds. In an embodiment, the hydrodealkylation inlet stream 213 contains less than 70 wt. % of di-aromatic compounds. In an embodiment, the hydrodealkylation inlet stream 213 contains less than 50 wt. % of di-aromatic compounds. In an embodiment, the hydrodealkylation inlet stream 213 contains less than 40 wt. % of di-aromatic compounds. In an embodiment, the hydrodealkylation inlet stream 213 contains less than 20 wt. % of di-aromatic compounds. In an embodiment, the hydrodealkylation inlet stream 213 contains less than 10 wt. % of di-aromatic compounds. In an embodiment, the hydrodealkylation inlet stream 213 contains less than 1 wt. % of di-aromatic compounds.

In the embodiment of FIG. 2, aromatic bottoms stream 204, admixed with the hydrogen stream 206, now stream 213, is supplied to hydrodealkylation reactor 218 along a steam stream 222, and a sulfur-containing compound stream 224, for example a sulfur-containing compound stream that can decompose to yield hydrogen sulfide, for example disulfide oils with 2 to 10 carbon number, for example dimethyldisulfide. In an embodiment, the sulfur-containing compound stream 224 is substituted by a disulfide oil stream commonly produced in a MEROX unit. Hydrodealkylation inlet stream 213 is processed in hydrodealkylation reactor 218 to produce a hydrodealkylated stream 226 containing hydrogen, $C_1$ to $C_4$ gases, benzene, toluene, xylenes, and residual $C_{9+}$ compounds. In certain embodiments, this hydrodealkylated stream 226 is sent to separation unit 228 to obtain a top product stream 230 containing hydrogen, $C_1$ to $C_4$ gases, benzene, toluene, and xylenes. The bottom product stream 232 from separation unit 228 is either removed as a bleed stream 234 or sent to the outlet of the aromatic recovery complex 202 as a recycle stream 238 to be directed back to the outlet of aromatic recovery complex 202 to return to hydrodealkylation reactor 218. In certain embodiments, the top product stream 230 is sent to a fractionator to separate $C_1$ to $C_4$ gases and BTX. The BTX can be supplied to an aromatics fractionation unit to produce a benzene-rich stream and a stream containing the xylenes that can be processed to recover xylenes.

Figure 3:
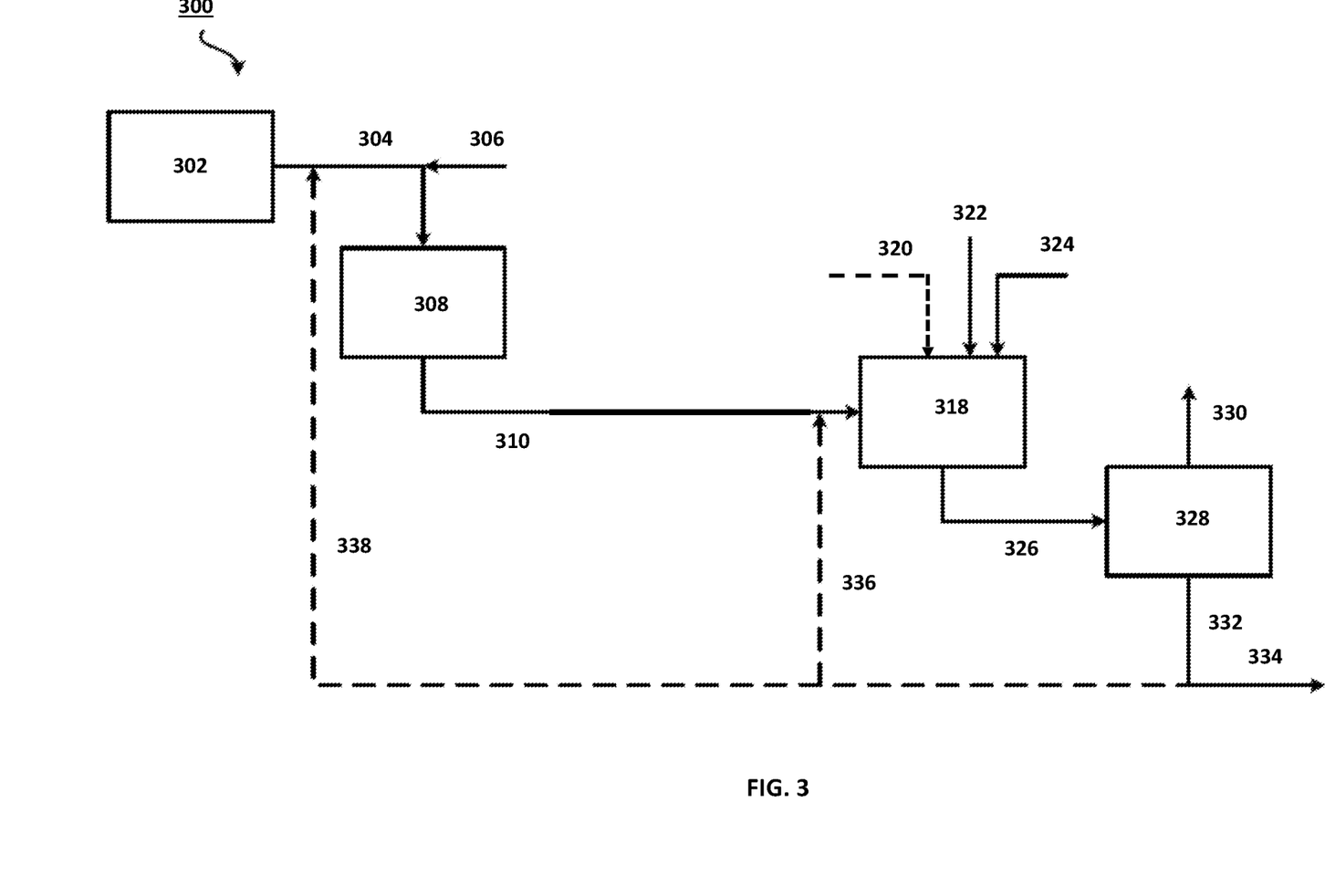
FIG. 3 is a schematic representation of integrated hydrodearylation and hydrodealkylation components of an aromatics processing system.

In an embodiment 300 as described in FIG. 3, an aromatic bottoms stream 304 from an aromatic recovery complex 302 and a hydrogen stream 306 are directed to a hydrodearylation reactor 308 for processing into a hydrodearylated stream 310. In some embodiments (not pictured) hydrogen gas can be dissolved in stream 304 and sent to a flash separator to leave only hydrogen dissolved in the liquid stream and any excess hydrogen gas recycled. In an embodiment, the hydrodearylated stream 310 contains greater than 10 wt. % of alkyl mono-aromatic compounds. In an embodiment, the hydrodearylated stream 310 contains greater than 20 wt. % of alkyl mono-aromatic compounds. In an embodiment, the hydrodearylated stream 310 contains greater than 40 wt. % of alkyl mono-aromatic compounds. In an embodiment, the hydrodearylated stream 310 contains about 50 wt. % of alkyl mono-aromatic compounds. In an embodiment, the hydrodearylated stream 310 contains about 70 wt. % of alkyl mono-aromatic compounds.

In an embodiment, the hydrodearylated stream 310 contains about 90 wt. % of alkyl mono-aromatic compounds. In an embodiment, the hydrodearylated stream 310 contains less than 70 wt. % of di-aromatic compounds. In an embodiment, the hydrodearylated stream 310 contains less than 50 wt. % of di-aromatic compounds. In an embodiment, the hydrodearylated stream 310 contains less than 40 wt. % of di-aromatic compounds. In an embodiment, the hydrodearylated stream 310 contains less than 20 wt. % of di-aromatic compounds. In an embodiment, the hydrodearylated stream 310 contains less than 10 wt. % of di-aromatic compounds. In an embodiment, the hydrodearylated stream 310 contains less than 1 wt. % of di-aromatic compounds.

The hydrodearylated stream 310 is supplied to a hydrodealkylation reactor 318 along with an optional hydrogen stream 320, a steam stream 322, and a sulfur-containing compound stream 324, for example a sulfur-containing compound stream that can decompose to yield hydrogen sulfide, for example disulfide oils with 2 to 10 carbon number, for example dimethyldisulfide. In an embodiment, the sulfur-containing compound stream 324 is substituted by a disulfide oil stream commonly produced in a MEROX unit. Hydrodearylated stream 310 is processed in the hydrodealkylation reactor 318 to produce a hydrodealkylated stream 326 containing hydrogen, $C_1$ to $C_4$ gases, benzene, toluene, xylenes, and residual $C_{9+}$ compounds. In certain embodiments, this hydrodealkylated stream 326 is sent to a second separation unit 328 to obtain a top product stream 330 containing hydrogen, $C_1$ to $C_4$ gases, benzene, toluene, and xylenes. The bottom product stream 332 from second separation unit 328 is either removed as a bleed stream 334 or sent to the hydrodealkylation reactor 318 as a first recycle stream 336 or sent to the hydrodearylation reactor 308 as a second recycle stream 338. In certain embodiments, the top product stream 330 is sent to a fractionator to separate $C_1$ to $C_4$ gases and BTX. The BTX can be supplied to an aromatics fractionation unit to produce a benzene-rich stream and a stream containing the xylenes that can be processed to recover xylenes.

In various embodiments, the lighter hydrocarbon stream may be processed to provide a recycled hydrogen stream. In various embodiments, the recycled hydrogen stream may be combined with a makeup hydrogen stream to provide the hydrogen stream to be supplied to the hydrodearylation and hydrodealkylation reactors.

In various embodiments, the lighter hydrocarbon stream may be processed to provide a recycled hydrogen stream. In various embodiments, the recycled hydrogen stream may be combined with a makeup hydrogen stream to provide the hydrogen stream to be supplied to the Hydrodearylation and hydrodealkylation reactors.

EXAMPLE

Methods and systems for integration of a hydrodearylation process with a hydrodealkylation process are illustrated here. While the particular example provided below is for a stream containing $C_{9+}$ compounds, the methods and systems for integration of a hydrodearylation process with a hydrodealkylation process can utilize a $C_{10+}$, or $C_{11+}$ feed. The properties and composition of an aromatics bottoms stream from an aromatics complex are provided in Tables 1 and 2. The aromatics bottoms stream has a density of about 0.8838 grams per cubic centimeter. The boiling point properties of the feed stream determined using the ASTM D2892 method are shown in Table 1.

TABLE 1

| Property | Boiling Point, ° C. |
| --- | --- |
| Initial Boiling Point | 153 |
| 5 wt. % | 162 |
| 10 wt. % | 163 |
| 30 wt. % | 167 |
| 50 wt. % | 172 |
| 70 wt. % | 176 |
| 90 wt. % | 191 |
| 95 wt. % | 207 |
| Final Boiling Point | 333 |

Composition of the aromatics bottoms stream is shown in Table 2.

TABLE 2

| Compounds | Weight percent % |
| --- | --- |
| Paraffins | 0.00 |
| Mono-aromatics | 94.1 |
| Naphtheno Mono-aromatics | 0.9 |
| Diaromatics | 3.8 |
| Naphtheno Di-aromatics | 0.9 |
| Tri+ aromatics | 0.3 |

Although the aromatics bottoms stream contained 94.1 wt. % of monoaromatics, it contained no BTX. The aromatics bottoms stream was subjected to non-catalytic thermal hydrodealkylation at a pressure of 40 bars, a temperature of 500° C., and a residence time of 393 seconds in a plug-flow tubular reactor. The hydrodealkylated stream had 1.8 wt. % Benzene.

The aromatics bottoms stream was subjected to non-catalytic hydrodealkylation. Since the aromatics bottoms stream contains no BTX, this stream is the same as if the aromatics bottoms stream was hydrodearylated and the hydrodearylated product stream sent to a separator to separate BTX and gases, with the $C_{9+}$ components thereafter being directed to the hydrodealkylation unit.

In either case, the hydrodealkylation unit is receiving a stream rich in $C_{9+}$ components. The only difference would be that in the case of the aromatics bottoms stream being hydrodearylated, there would be less volume being directed to the hydrodealkylation unit, when compared with sending the aromatics bottoms stream directly to the hydrodealkylation unit, however, in both cases, compositionally they are the same.

Reactions have been modeled and data fitted to calculate the kinetic parameters to estimate the BTX production at higher temperatures and shorter residence times. The results are shown below in Table 3.

TABLE 3

| Temperature, ° C. | Residence Time, sec | Benzene yield, Wt. % |
| --- | --- | --- |
| 600 | 20 | 0.8 |
| 650 | 20 | 5.3 |
| 700 | 20 | 26.7 |
| 600 | 40 | 1.5 |
| 650 | 40 | 10.3 |
| 700 | 40 | 46.2 |

Ranges may be expressed herein as from about one particular value and to about another particular value. When such a range is expressed, it is to be understood that another embodiment is from the one particular value and/or to the other particular value, along with all combinations within said range. Where the range of values is described or referenced here, the interval encompasses each intervening value between the upper limit and the lower limit as well as the upper limit and the lower limit and includes smaller ranges of the interval subject to any specific exclusion provided. Where a method comprising two or more defined steps is recited or referenced herein, the defined steps can be carried out in any order or simultaneously except where the context excludes that possibility. While various embodiments have been described in detail for the purpose of illustration, they are not to be construed as limiting, but are intended to cover all the changes and modifications within the spirit and scope thereof. The term about as used herein includes plus or minus 5% of the value provided.

That claimed is:

1. A process for production of benzene, toluene, and xylenes, the process comprising the steps of:
supplying a hydrogen stream and a feed stream containing one or more of heavy alkyl aromatic compounds and alkyl-bridged non-condensed alkyl multi-aromatic compounds from an aromatic complex to a hydrodearylation reactor operating in a temperature range of about 200° C. to about 450° C. to react in the presence of a catalyst under specific reaction conditions to yield a hydrodearylated stream containing hydrogen, $C_1$ to $C_4$ gases, benzene, toluene, xylenes, and $C_{9+}$ compounds;
supplying the hydrodearylated stream to a first separation unit to produce a bottom separated stream containing $C_9+$ compounds and a top separated stream containing hydrogen, $C_1$ to $C_4$ gases, benzene, toluene, and xylenes;
supplying a hydrogen stream and the bottom separated stream containing $C_9+$ compounds to a hydrodealkylation reactor operating in a temperature range of about 500° C. to about 900° C. to produce a hydrodealkylated stream containing $H_2$, $C_1$ to $C_4$ gases, benzene, toluene, xylenes, and $C_9+$ compounds; and
supplying the hydrodealkylated stream to a second separation unit to produce a bottom product stream containing unconverted $C_9+$ compounds and a top product stream containing hydrogen, $C_1$ to $C_4$ gases, benzene, toluene, and xylenes.

2. The process of claim 1, wherein the hydrodealkylation reactor is a non-catalytic thermal hydrodealkylation reactor.

3. The process of claim 1, wherein the top product stream is supplied to an aromatic fractionation unit to produce a benzene-rich stream, a toluene-rich stream, and a xylene-rich stream.

4. The process of claim 1, wherein a sulfur-containing compound stream is supplied to the hydrodealkylation reactor.

5. The process of claim 1, wherein a steam stream is supplied to the hydrodealkylation reactor.

6. The process of claim 1, wherein the bottom product stream is recycled to the hydrodealkylation reactor.

7. The process of claim 1, wherein the bottom product stream is recycled to the hydrodearylation reactor.

8. The process of claim 1, wherein the feed stream is from a xylene rerun column of an aromatic recovery process.

9. The process of claim 1, wherein the catalyst includes a support being at least one member of the group consisting of silica, alumina, titania, and combinations thereof, and further includes an acidic component being at least one member of the group consisting of amorphous silica-alumina, alumina, zeolite, and combinations thereof.

10. The process of claim 1, wherein conditions in the hydrodearylation reactor include an operating pressure in the range of about 5 bar gauge to 80 bar gauge.

11. The process of claim 1, wherein a volumetric ratio of hydrogen to the hydrocarbon components in the hydrodearylation reactor ranges from 50 to 2500 $Nm^3/m^3$.

12. The process of claim 1, wherein conditions in the hydrodealkylation reactor include an operating hydrogen partial pressure in the range of about 5 bar gauge to 100 bar gauge.

13. The process of claim 1, wherein a molar ratio of hydrogen to the hydrocarbon components in the hydrodealkylation reactor ranges from 1 to 20.

14. A process for production of benzene, toluene, and xylenes, the process comprising the steps of:
supplying a hydrogen stream and a feed stream containing one or more of heavy alkyl aromatic compounds and alkyl-bridged non-condensed alkyl multi-aromatic compounds from a xylene rerun column of an aromatic recovery process to a hydrodealkylation reactor operating in a temperature range of about 500° C. to about 900° C. to react under specific reaction conditions to yield a hydrodealkylated stream containing hydrogen, $C_1$ to $C_4$ gases, benzene, toluene, xylenes, and $C_9+$ compounds; and
supplying the hydrodealkylated stream to a separation unit to produce a bottom product stream containing unconverted $C_9+$ compounds and a top product stream containing hydrogen, $C_1$ to $C_4$ gases, benzene, toluene, and xylenes.

15. The process of claim 14, wherein the hydrodealkylation reactor is a non-catalytic thermal hydrodealkylation reactor.

16. The process of claim 14, wherein the top product stream is supplied to an aromatic fractionation unit to produce a benzene-rich stream, a toluene-rich stream, and a xylene-rich stream.

17. The process of claim 14, wherein a sulfur-containing compound stream is supplied to the hydrodealkylation reactor.

18. The process of claim 14, wherein a steam stream is supplied to the hydrodealkylation reactor.

19. The process of claim 14, wherein the bottom product stream is recycled to an outlet of the aromatic complex.

20. The process of claim 14, wherein conditions in the hydrodealkylation reactor include an operating hydrogen partial pressure in the range of about 5 bar gauge to 100 bar gauge.

21. The process of claim 14, wherein a molar ratio of hydrogen to the hydrocarbon components in the hydrodealkylation reactor ranges from 1 to 20.

22. A process for production of benzene, toluene, and xylenes, the process comprising the steps of:
supplying a hydrogen stream and a feed stream containing one or more of heavy alkyl aromatic compounds and alkyl-bridged non-condensed alkyl multi-aromatic compounds from an aromatic complex to a hydrodearylation reactor operating in a temperature range of about 200° C. to about 450° C. to react in the presence of a catalyst under specific reaction conditions to yield a hydrodearylated stream containing hydrogen, $C_1$ to $C_4$ gases, benzene, toluene, xylenes, and $C_9+$ compounds;
supplying the hydrodearylated stream containing $C_9+$ compounds to a hydrodealkylation reactor operating in a temperature range of about 500° C. to about 900° C. to produce a hydrodealkylated stream containing $H_2$, $C_1$ to $C_4$ gases, benzene, toluene, xylenes, and $C_9+$ compounds; and
supplying the hydrodealkylated stream to a separation unit to produce a bottom product stream containing unconverted $C_9+$ compounds and a top product stream containing hydrogen, $C_1$ to $C_4$ gases, benzene, toluene, and xylenes.

23. The process of claim 22, further comprising the step of supplying a hydrogen stream to the hydrodealkylation reactor.

24. The process of claim 22, wherein the feed stream is from a xylene rerun column of an aromatic recovery process.

25. The process of claim 22, wherein conditions in the hydrodearylation reactor include an operating pressure in the range of about 5 bar gauge to 80 bar gauge.

26. The process of claim 22, wherein conditions in the hydrodealkylation reactor include an operating hydrogen partial pressure in the range of about 5 bar gauge to 100 bar gauge.

27. The process of claim 22, wherein the catalyst includes a support being at least one member of the group consisting of silica, alumina, titania, and combinations thereof, and further includes an acidic component being at least one member of the group consisting of amorphous silica-alumina, alumina, zeolite, and combinations thereof.

* * * * *